United States Patent [19]
Jeffers et al.

[11] 4,002,059
[45] Jan. 11, 1977

[54] APPARATUS FOR MANIPULATING CORROSION COUPONS AND THE LIKE

[75] Inventors: Mark A. Jeffers, Kenner; Jackie D. Dendy, Lafayette, both of La.

[73] Assignee: Standard Oil Company, Chicago, Ill.

[22] Filed: Feb. 18, 1976

[21] Appl. No.: 659,183

[52] U.S. Cl. .................................................. 73/86
[51] Int. Cl.² ........................................ G01N 17/00
[58] Field of Search ............ 73/86, 432 R; 138/104; 166/84, 75, 214

[56] References Cited
UNITED STATES PATENTS

| | | | |
|---|---|---|---|
| 3,174,332 | 3/1965 | Echtler et al. | 73/86 |
| 3,718,034 | 2/1973 | Swearingen | 73/86 |

*Primary Examiner*—James J. Gill, Jr.
*Assistant Examiner*—Anthony V. Ciarlante
*Attorney, Agent, or Firm*—Richard A. Stoltz

[57] ABSTRACT

A static monitoring device (such as a corrosion coupon manipulating apparatus for petroleum pipelines is described which allows the monitoring device to be run in and later pulled out without depressurizing the pipeline. Part of the apparatus can be removed while the monitoring device is in the pipeline, thus greatly reducing the likelihood of damage to the apparatus and pipeline. The removal of a portion of the apparatus also allows this portion to be reused to manipulate monitoring devices at different locations.

3 Claims, 2 Drawing Figures

APPARATUS FOR MANIPULATING CORROSION COUPONS AND THE LIKE

BACKGROUND OF THE INVENTION

This invention relates to petroleum (oil and/or gas) pipelines and especially to insert and remove static monitoring devices in pipelines under pressure using wireline tools.

Wireline tools are commercially available and have been used to insert and withdraw various devices in conjunction with oil wells for many years. Wireline device uses include the insertion of instruments for measuring downhole pressure or temperature. Other uses also include the downhole mounting of pressure and flow control devices such as chokes and check valves.

In mounting a choke in a well, for example, the choke can be attached to a locking device and both attached to a running tool in the wireline lubricator. The lubricator is then mounted on top of a valve on the wellhead. The valve is opened and the locking device and choke are lowered into position and locked in place, typically in a seating (or landing) nipple which had previously been placed in an appropriate position. As the locking device and choke are locked in place, they are disengaged from the running tool (typically by a strong pull on the wireline after the locking device has been locked in the seating nipple). The running tool is then pulled up into the lubricator and the valve closed. The pressure can then be bled down and the lubricator disconnected from the wellhead.

If the choke is to be removed at some later time, the lubricator is remounted on top of the valve on the wellhead with a pulling tool (often a different tool than the running tool) inside of the lubricator. The valve is then opened and the tool lowered to engage the locking device and choke. The pulling tool unlocks the locking device from the nipple and the wireline is then used to pull the locking device back up into the lubricator. The valve is then closed and the lubricator pressure bled down. The lubricator with the retrieved locking device and choke may then be removed from the wellhead.

Lubricators, locking devices, running tools, landing nipples, and pulling tools are shown, for example, in the following U.S. Pat. No. 2,677,427, issued to McKinney et al., on May 4, 1954; U.S. Pat. No. 3,207,222, issued to Tamplen on Sept. 21, 1965; U.S. Pat. No. 2,887,163, issued to McGowen et al., on May 19, 1959; U.S. Pat. No. 2,920,704, issued to Fredd on Jan. 12, 1960; U.S. Pat. No. 3,294,173 issued to Hodges on Dec. 27, 1966.

Corrosion coupons have been inserted into pipelines, both with the line depressurized and under pressure. The depressurization of the pipeline at any time which coupons are to be inserted or retrieved is, of course, inconvenient and expensive.

One method of inserting coupon assemblies into a pipeline under pressure is by use of a hydraulic insertion mechanism such as shown in U.S. Pat. No. 3,718,034, issued to Swearingen on Feb. 27, 1973. Such a mechanism must remain mounted on the pipeline during the entire time the coupon assembly is inserted and thus each coupon assembly requires one complete mechanism. In addition, the mechanism is relatively thin and fairly tall (typically sticking up about 4 feet or more above the pipeline) and is very susceptible to damage, especially when left in an isolated location.

As an alternative to a hydraulic force for insertion, mechanisms such as a lead screw and crank can be used to supply the required force. Such mechanisms also remain mounted throughout the test and are generally even taller and thus more susceptible to damage.

SUMMARY OF THE INVENTION

The apparatus of this invention is for use with petroleum pipelines and can be used to insert and withdraw static monitoring devices without depressuring the pipeline. The apparatus includes a valve mounted generally on top of the pipeline, a lock receiving section mounted on the valve, a wireline lock means adapted to be fastenable in the lock receiving section, and a monitoring device such as a corrosion coupon assembly mounted on the bottom of the lock means in such a manner that when the lock means is fastened in the lock receiving station, the monitoring device assembly extends down through said valve and into the pipeline. The apparatus also includes at least one wireline lock-gripping tool to controllably grip the lock means, an isolation valve mounted on top of the lock receiving station, and a wireline lubricator fastened on top of the isolation valve. The wireline lubricator is adapted to be unfastened from the isolation valve and removed while the monitor is in the pipeline.

One advantage of this apparatus is that it can be assembled from commercially available parts. The apparatus has the further advantages (resulting from its major portion being removable) that the susceptibility to damage is greatly reduced and that the removable portion can be used to service many different monitoring locations.

BRIEF DESCRIPTION OF THE DRAWINGS

The invention will be further decribed by reference to the drawings, in which.

DESCRIPTION OF THE PREFERRED EMBODIMENTS

Figure 1:
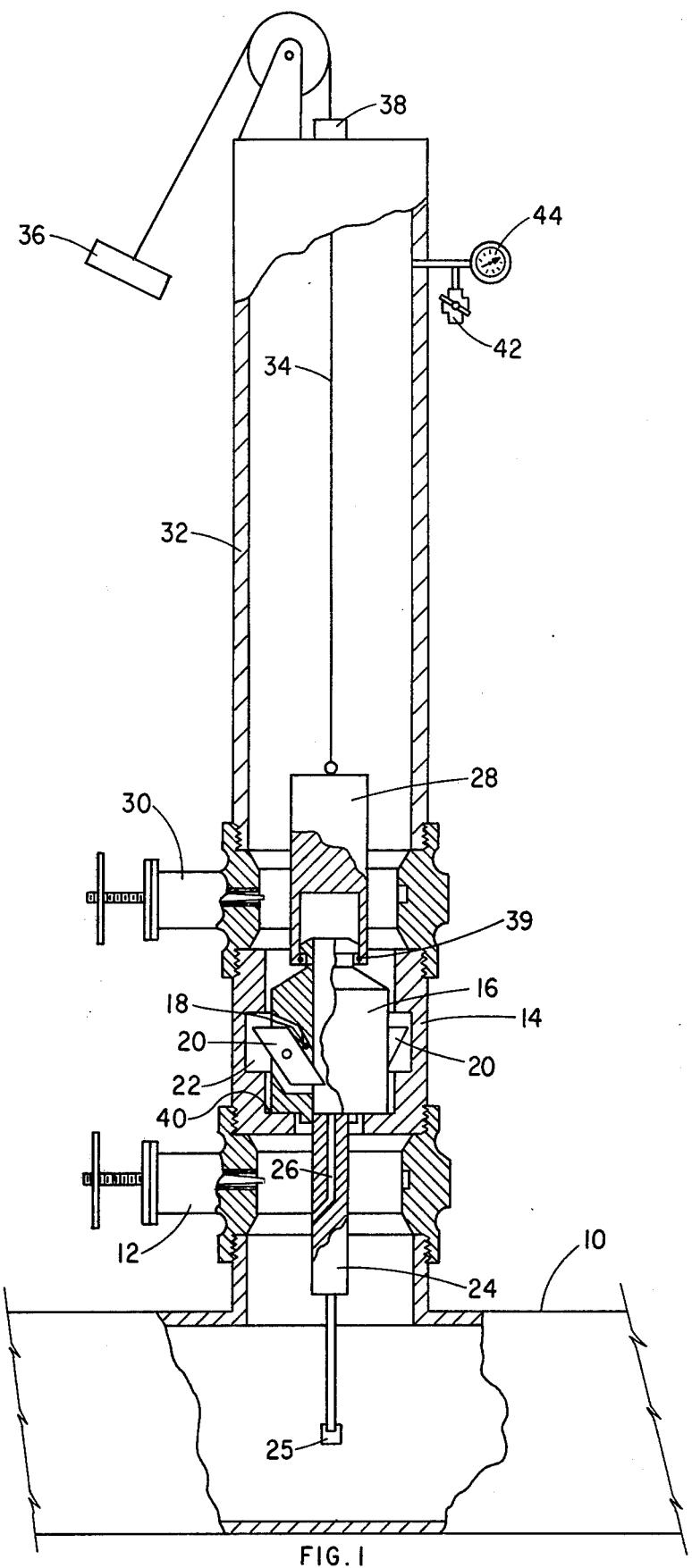
FIG. 1 is an elevation, partly in section, of a pipeline with the apparatus of this invention.

FIG. 1 generally illustrates the equipment of this invention with a corrosion coupon inserted prior to withdrawal of the running tool. The oil or gas pipeline 10 with its previously existing gate valve 12 on top of the line, is shown with a lock receiving section 14 added on top of the valve 12. The wireline lock means 16 is shown locked in place inside the lock receiving secton 14. A spring 18 holds each locking dog 20 out into the groove 22 in the lock receiving section (or seating nipple) 14. The corrosion coupon assembly 24 is mounted on the bottom of the lock means 16 and extends down through valve 12 to locate the coupon 25 in the pipeline 10. A pressure equalizing passageway 26 is provided so that the pipeline fluid can flow up through the center of the wireline lock means (or locking device) 16 to avoid any pressure differential across the locking device 16 which might cause problems when the device 16 is unlocked just prior to retrieval. The wireline lock-gripping tool (here a running tool 28) is shown engaged with the lock device 16. The isolation valve 30 is mounted on top of the seating nipple 14 and the wireline lubricator 32 is mounted on top of the isolation valve 30.

To begin the coupon insertion, the lubricator 32, isolation valve 30, and seating nipple 14 are assembled and the running tool 28, locking device 16, and coupon assembly 24 are attached to the wire 34 and pulled by the wireline handle 36 up into the lubricator 32 (the wire 34 passing through a packing gland 38 on top of the lubricator 32). This equipment is then mounted on top of the pipeline valve 12. The pipeline valve 12 is then opened. The wire, which has previously been fastened to hold the running tool 28, locking device 16, and coupon assembly 24 up in the lubricator 32 is released and, controlled by the handle 36 to lower the assembly into place with the locking device 16 setting on the bottom shoulder 40 of the seating nipple 14 and the spring 18 pushing the dogs 20 out into the groove 22 of the seating nipple 14. Sinker weights can be added with the running tool 28, if necessary to obtain enough weight on the running tool 28 to cause it to lower properly. A strong pull on the wireline handle 30 causes the running tool 28 to shear loose at the shear ring 39 and thus separate from the locking device 16. Further pulling on the wire handle 36 withdraws the running tool 28 up into the lubricator 32. The isolation valve 30 is then closed and the pressure in the lubricator 32 is bled down by vent valve 42. When the pressure gauge 44 indicates that atmospheric pressure has been obtained in the lubricator 32, the lubricator 32 (with the running tool 28 inside) can be disconnected from the isolation valve 30. Once the lubricator 32 has been removed, the remaining equipment is typically less than 2 feet high and is not easily damaged.

The same lubricator and running tool can, of course, then be used to insert other static monitoring devices at other locations. The static monitoring devices can, of course, be devices other than corrosion coupons as for example, erosion test coupons or particulate collection filters can be similarly manipulated. While wireline tools could also be used to insert dynamic monitoring devices (generally devices which use electrical wires to transmit signals), the primary advantages of this invention are lost in such cases. The lubricator must remain in place in the pipeline valve throughout such tests, as the electrical connections come out through the packing on top of the lubricator.

Figure 2:
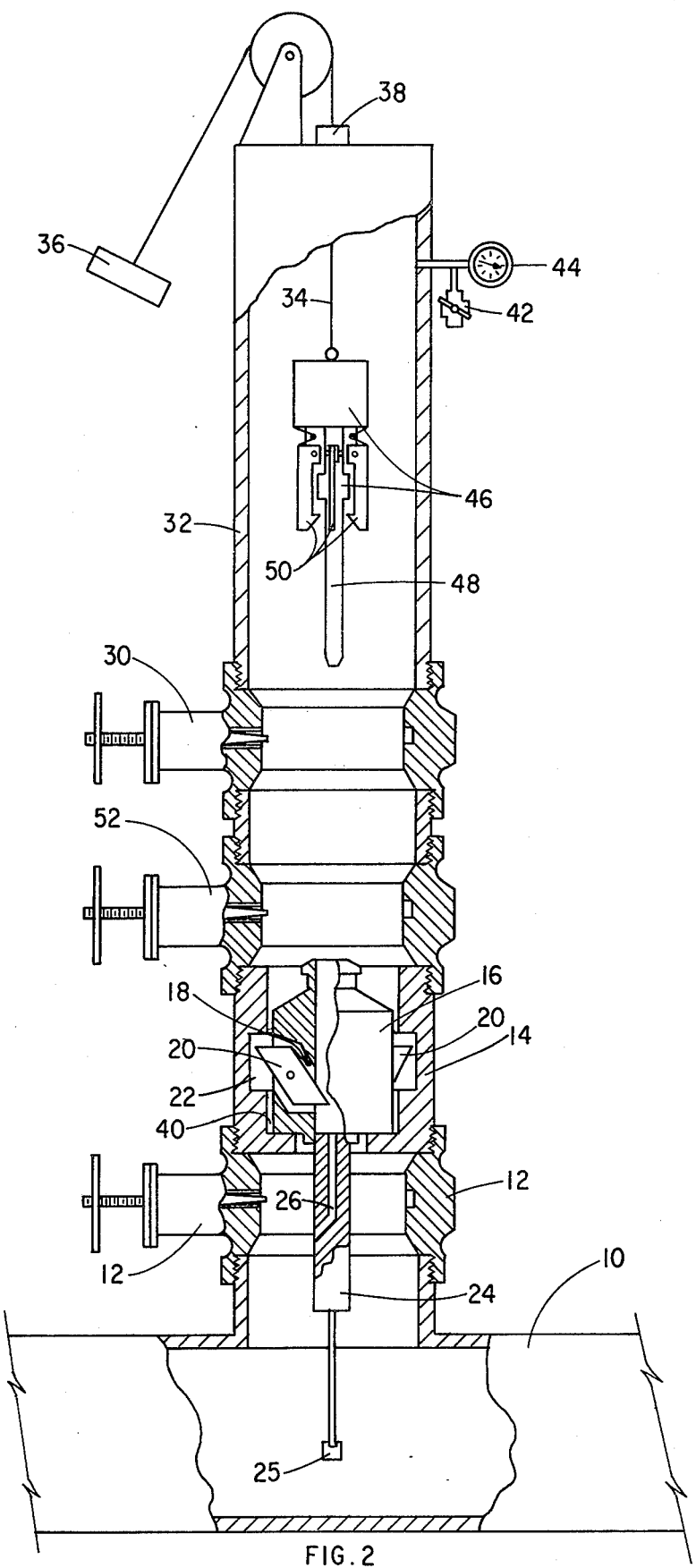
FIG. 2 is an elevation, again partly in section, of a configuration which includes a safety valve.

FIG. 2 shows a pulling tool 46 as the wireline lock-gripping tool in the lubricator 32. The lubricator 32 would be replaced atop the isolation valve 30 when the coupon (or other static monitoring device) was to be removed (typically months or in some cases even years after insertion). Here the pulling tool 46 has a probe 48 which, when tool 46 is lowered, will contact the dogs 20, cause them to come out of the seating nipple grooves 22, so that when the pulling tool arms 50 engage the top of the locking device 16, the coupon assembly 24 and the pulling tool 46 can all be drawn up into the lubricator 32. The pipeline valve 12 can then be closed, the lubricator pressure bled down, and all of the apparatus above the pipeline valve 12 removed.

The foregoing description of the operation is, of course, merely generally illustrative of the principles involved. Commercial wireline tools vary in design and the construction of any particular tools will differ somewhat from that described. Some commercial tools, for example, use the same tool with a minor modification both to run and to pull (inserting a ring, for example, to control when the tool grips the lock means 16).

FIG. 2 also illustrates the use of a safety valve 52. The use of this additional valve 52 is preferred for safety reasons. This valve 52 is generally left open but can be closed when the lubricator is removed and periodically opened to check for leakage past valve 30. If the isolation valve 30 starts to leak with a monitoring device in place after the lubricator 32 has been removed, the safety valve 52 can be closed and the isolation valve 30 can be replaced without shutting off the pipeline 10. Another use of the safety valve 52 is provided when the isolation valve 30 does not close properly after the insertion of a monitoring device while the lubricator 32 is still in place. In the absence of a safety valve 52 there would be no way to remove the lubricator 32 and replace the leaky valve without shutting down the pipeline 10. This is because the pipeline valve 12 cannot be closed with the coupon assembly 24 in place and commercial running tools 28 cannot generally be used to pull the locking device 16 so that the coupon assembly 24 cannot be pulled out of the pipeline 10 and the pipeline valve 12 up into the lubricator 32. Closing the safety valve 52 allows the lubricator 32 to be removed and also allows the isolation valve 30 to be replaced. The pipeline valve 12, the isolation valve 30, and the safety valve 52 are all shown as gate vales. Other types of valves which will allow objects to pass through (such as ball valves) could also be used.

The invention is not to be construed as limited to the particular forms described herein, since these are to be regarded as illustrative rather than restrictive. The invention is intended to cover all configurations which do not depart from the spirit and scope of the invention.

We claim:
1. A static monitoring device manipulating apparatus for petroleum pipeline, a portion of which apparatus can be removed while the monitoring device is in said pipeline, said apparatus comprising:
   a. a pipeline valve mounted generally on top of said pipeline;
   b. a lock receiving section mounted on top of said pipeline valve;
   c. a wireline lock means adapted to be fastenable in said lock receiving section;
   d. a static monitoring device assembly mounted on the bottom of said lock means in such a manner that when said lock means is fastened in said lock receiving section that said static monitoring device assembly extends down through said pipeline valve and into said pipeline;
   e. at least one wireline lock gripping tool to controllably grip said lock means;
   f. an isolation valve mounted on top of said lock receiving section; and
   g. a wireline lubricator fastened on top of said isolation valve, said wireline lubricator being adapted to being unfastened from said isolation valve while said static monitoring device assembly is extending into said pipeline.

2. The apparatus of claim 1, wherein a safety valve is mounted between said isolation valve and said lock receiving section.

3. Petroleum pipeline equipment comprising:
   a. a petroleum pipeline;
   b. a pipeline valve mounted generally on top of said pipeline;
   c. a lock receiving section mounted on top of said pipeline valve;

d. a wireline lock means adapted to be fastenable in said lock receiving section;

e. a static monitoring device assembly mounted on the bottom of said lock means in such a manner that when said lock means is fastened in said lock receiving section that said static monitoring device assembly extends down through said pipeline valve and into said pipeline;

f. at least one wireline lock gripping tool to controllably grip said lock means;

g. an isolation valve mounted on top of said lock receiving section; and h. a wireline lubricator removably fastened on top of said isolation valve, said lubricator being adapted to be fastened to manipulate said static monitoring device assembly on said isolation valve, and to be removable while said monitoring device assembly is extending into said pipeline.

* * * * *